United States Patent [19]

Ingber et al.

[11] Patent Number: 5,125,839
[45] Date of Patent: Jun. 30, 1992

[54] DENTAL IMPLANT SYSTEM

[76] Inventors: Abraham Ingber, 9249 Cambridge Manor Ct., Potomac, Md. 20854; Vincent Prestipino, 14448 Long Channel Cir., Germantown, Md. 20874; Anopet Phimmasone, 6008-F Curtier Dr., Alexandria, Va. 22310

[21] Appl. No.: 589,263

[22] Filed: Sep. 28, 1990

[51] Int. Cl.⁵ .............................................. A61C 13/28
[52] U.S. Cl. .................................... 433/169; 433/173
[58] Field of Search ............... 433/169, 173, 174, 175, 433/176

[56] References Cited

U.S. PATENT DOCUMENTS 4,560,353  12/1985  Schulte et al. ................... 433/176
4,850,870  7/1989  Lazzara et al. ................... 433/173
4,872,839  10/1989  Brajnovic ....................... 433/174

FOREIGN PATENT DOCUMENTS 2717506  5/1978  Fed. Rep. of Germany ...... 433/173

Primary Examiner—Cary E. O'Connor

[57] ABSTRACT

A bone-embedded implant fixture is interfaced with an aluminum oxide abutment post through which a variety of different arrangements and types of prosthesis superstructures may be supported, including those having separate coping portions surface bonded to the abutment post. An access bore in the abutment post accomodates threaded insertion of a screw fastener carrying a deformable washer to hold the dental implant assembled and seal the gum tissue region into which the abutment post is fitted.

27 Claims, 2 Drawing Sheets

1

DENTAL IMPLANT SYSTEM

BACKGROUND OF THE INVENTION

This invention relates generally to improvements in the formation and installation of dental implants, and more particularly to dental implants having a metallic bone-embedded fixture with which a post is interfaced to support a prosthesis superstructure.

Surgical techniques for implantation of dental prostheses by means of a metallic bone-embedded fixture are well known as disclosed for example in U.S. Pat. Nos. 4,824,372, 4,872,839 and 4,934,935 to Jorneus et al., Brajnovic and Edwards, respectively. According to the Jorneus et al. and Brajnovic patents, a titanium bone-embedded fixture is interfaced with a metallic abutment post, on which the superstructure is supported, the post having an internally shouldered access bore through which a screw fastener is inserted to axially hold the implant components assembled. Various problems and restrictions arise, however, in the attachment and retention of superstructures to such abutment posts.

U.S. Pat. No. 4,850,870 to Lazzara et al. is directed to specific examples of attachment and retention of superstructure on metallic abutment posts interfaced with bone-embedded implant fixtures to which the posts are secured by screw fasteners. The superstructure according to the Lazzara et al. patent includes a separate coping portion secured by means of another screw fastener to the core portion of the abutment post.

U.S. Pat. No. 4,304,553 to Heinke et al. is also of interest because it discloses a superstructure support post made of aluminum oxide. However, such post is formed integral with the bone-embedded fixture so as to introduce various problems affecting installational flexibility and implant adjustment or repair.

It is therefore an important object of the present invention to provide an improved dental implant assembly and an associated installational procedure to facilitate customized formation and fitting of dental prostheses with greater economy and flexibility.

A further object of the invention in accordance with the foregoing object is to provide a dental implant assembly that is less likely to be irreparably damaged and more readily repaired.

Yet another object of the invention is to provide a dental implant assembly having other desirable attributes not heretofore available, such as increased strength and more effective fluid sealing of the gum tissue region in which a separate abutment post is interfaced with the bone-embedded fixture to which it is attached by means of a screw fastener.

SUMMARY OF THE INVENTION

In accordance with the present invention, a ceramic post is interfaced with the receiving end portion of a metallic bone-embedded implant fixture to support a dental prosthesis superstructure. The support post is made of aluminum oxide so as to provide core strength as well as flexibility in the selection of superstructure arrangement and design to best meet installational requirements and patient needs. Such post mounts an anatomical shaped trans-tissue formation in abutment with the receiving end portion of the bone-embedded fixture within an interface region between the edentulous bone from which the fixture projects and the gingival edge of the gum tissue. A curved transition surface portion extends from the large diameter end of the trans-tissue abutment formation to an elongated cylindrical core portion of the post, cut to the desired length to accomodate a custom designed superstructure. Where the superstructure includes a separate coping portion made of porcelain for example, the coping portion is surface bonded without fastenings by a firing process, directly to the core portion of the post. Such firing process forms a unitary body in view of the interacting properties of the ceramic material and porcelain and without shrinkage as indicated for example in U.S. Pat. No. 4,585,417 to Sozio et al.

The abutment support post is formed with an aligned access bore through which a screw fastener is inserted and threaded into the bone-embedded implant fixture for attachment of the post thereto and to seal the interface region by means of a deformable washer spacing the head portion of the fastener from a shoulder on which it is seated within the access bore in the post according to certain embodiments of the invention. The washer surrounds a connecting shank portion of the fastener of minimum diameter and structural strength so that rupture of the dental implant will most likely occur at that location resulting in minimal damage to the dental implant assembly facilitating retrieval of parts and enabling easier repair.

BRIEF DESCRIPTION OF DRAWING FIGURES

The nature of the present invention will be more readily understood by reference to the accompanying drawing in which.

DETAILED DESCRIPTION OF PREFERRED EMBODIMENTS

Figure 1:
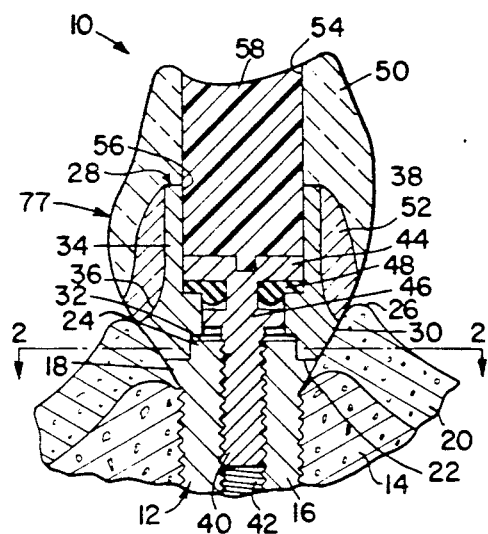
FIG. 1 is a section view of a dental implant installation in accordance with one embodiment of the invention.
Figure 2:
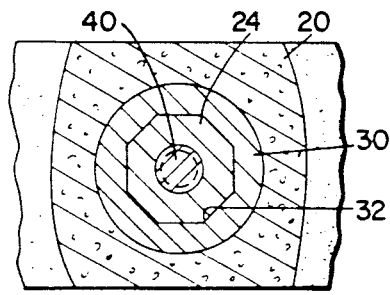
FIG. 2 is a transverse section view of the implant installation taken substantially through a plane indicated by section line 2—2 in FIG. 1.

Referring now to the drawing in detail, FIGS. 1 and 2 illustrate a typical implant assembly in accordance with one embodiment of the present invention, generally referred to by reference numeral 10. A metallic implant fixture 12 generally well known in the art and associated with the implant assembly 10 is embedded in edentulous bone 14 within a patient's mouth in accordance with surgical implantation techniques developed by Per-Ingvar Branemark et al., as referred to in the aforementioned U.S. patents to Jorneus et al., Brajnovic and Edwards. Such implant fixture is of titanium and includes an externally threaded body 16 within the bone from which a radially projecting flange portion 18 extends into the gum tissure 20 forming an abutment shoulder 22 about a cross-sectionally non-circular receiving end portion 24. The receiving end portion 24 of the implant fixture is thus exposed to an interfacing region between the edentulous bone 14 and the gingival edge 26 of the gum tissue as shown in FIG. 1.

With continued reference to FIGS. 1 and 2, an abutment support post generally referred to by reference numeral 28 is interfaced with the implant fixture 12 within the aforementioned interfacing region by engagement with the shoulder 22 at the small diameter end of a conical shaped trans-tissue abutting section 30 of the post. A cross-sectionally, non-circular socket opening 32 is formed within the trans-tissue section of the post dimensioned to match the receiving end portion 24 of the implant fixture with a sliding fit so as to prevent angular displacement of the post relative to the implant fixture when interfaced in axial alignment.

In accordance with the present invention, the support post 28 is made of a ceramic material such as aluminum oxide ($Al_2O_3$) so that it may be readily surface bonded, with or without adhesives, to a variety of different superstructure materials and arrangements on a supragingival section of the post which includes an axially elongated cylindrical core portion 34 as shown in FIG. 1. To enhance application and retention of the superstructure on the supragingival section of the post, an external shallow curved transition surface portion 36 interconnects the conical trans-tissue section 30 with the cylindrical core portion 34 which has a uniform diameter less than the maximum end diameter of the trans-tissue section 30.

When properly interfaced with the bone-embedded implant fixture, the support post is removably fastened to the implant fixture by means of a screw fastener generally referred to by reference numeral 38 in FIG. 1, to prevent axial disassembly. Thus, the screw fastener includes an externally threaded portion 40 treadedly inserted into an internally threaded bore 42 formed in the bone-embedded body portion 16 of the implant fixture. The threaded screw portion 40 of the fastener is connected to a radially enlarged head portion 44 by means of an intermediate shank portion 46 which extends from the head portion through the interface region into the receiving end portion 24 of the implant fixture. The intermediate shank portion 46 is operative to locationally limit implant rupture thereto and in cooperation with an annular washer 48 is effective to seal the interface region, as will be explained in detail hereinafter, in accordance with the present invention.

In accordance with one embodiment of the invention as illustrated in FIG. 1, the prosthesis superstructure supported on the post 28 includes a restoration tooth 50 directly bonded to a separate coping portion 52 made of porcelain material which may be surface bonded, without any fasteners, to the supragingival section of the post by a firing process to form a unitary body therewith. The coping portion 52 thus completely covers the supragingival core section of the post 28 as shown to firmly support the tooth 50 thereon. The tooth is furthermore formed with an access opening 54 in axial alignment with an axial bore 56 in the post 28 through which the screw fastener 38 is inserted. The implant assembly 10 is accordingly finished by insertion of a suitable filler resin 58 into the access opening and bore to cover the exposed head portion 44 of the fastener 38 and complete formation of the dental prosthesis.

Figure 3:
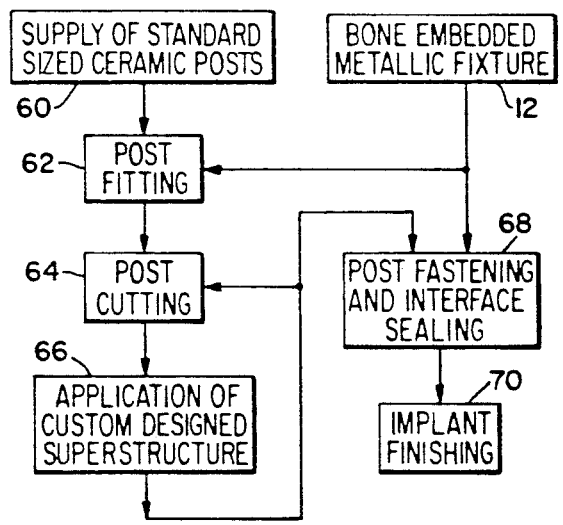
FIG. 3 is a block diagram depicting the procedure associated with formation and installation of dental implant assemblies, such as that shown in FIGS. 1 and 2, pursuant to the present invention.

The procedure involved in the customized formation of a dental implant assembly such as that illustrated in FIGS. 1 and 2, is outlined in the diagram of FIG. 3. As diagrammed in FIG. 3, a supply 60 of different standard sized prefabricated support posts made of aluminum oxide ceramic material is available for selection of a post to meet individual requirements of a post fitting operation 62 for dental patients within which titanium fixtures 12 have been implanted. The selected post is then cut to a desired axial length as denoted by diagram block 64 for application of a customized prosthesis superstructure to the post as denoted by block 66 in FIG. 3. The prothesis supporting post is then interfaced with the bone-embedded fixture and fastened thereto while also sealing the interface region as depicted by diagram block 68. The implant assembly is completed by a finishing step as denoted by block 70.

Figure 4:
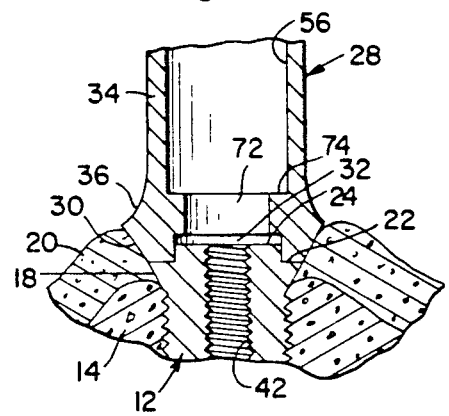
FIGS. 4–8 are section views showing formation and installation of the dental implant of FIGS. 1 and 2 in different stages of assembly.
Figure 5:
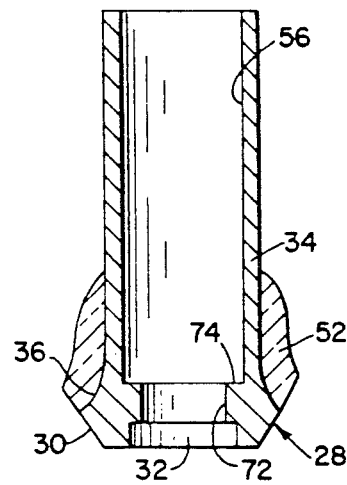
Figure 6:
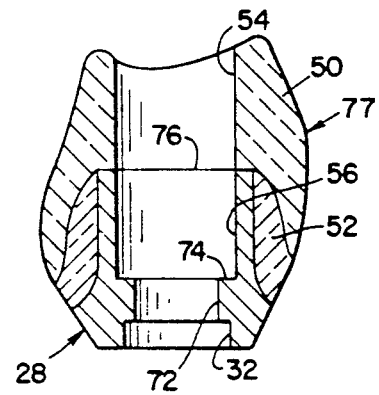

FIGS. 4-8 illustrate the implant assembly of FIGS. 1 and 2 in different stages of assembly to further explain the method outlined in FIG. 3 as well as to describe in detail the interface region sealing and rupture control aspects of the invention. The result of a post fitting step 62 is illustrated in FIG. 4, showing a selected post 28 interfaced with the bone-embedded fixture 12. The access bore 56 in the post is shown in communication with the socket 32 through a smaller diameter bore 72 to form an annular shoulder 74 in axially spaced relation to the socket 32. The fitted post is then removed from the patient for application of the prosthesis superstructure thereto as shown in FIGS. 5 and 6. Initially the porcelain coping portion 52 of the superstructure, as shown in FIG. 5, is applied to the post according to one embodiment by a surface bonding firing process as aforementioned. The support post may then be cut to remove the portion of the cylindrical supragingival core section projecting beyond the coping 52 and form a cut axial end 76 as shown in FIG. 6. The prosthesis tooth 50 is then applied as shown to form the superstructure 77 according to the illustrated embodiment to complete the step 66 as diagrammed in FIG. 3.

Figure 7:
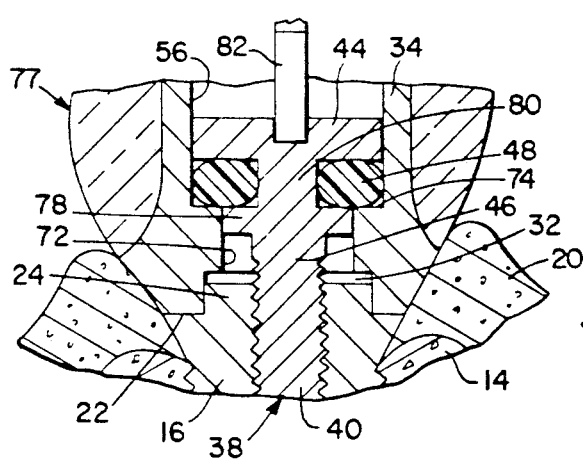
Figure 8:
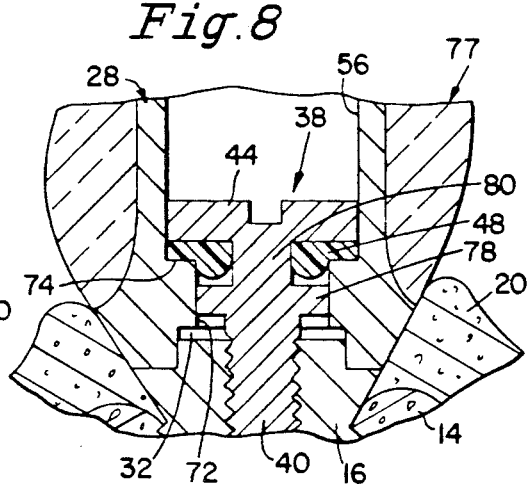

The post fastening and interface sealing step 68 diagrammed in FIG. 3 is performed as illustrated in FIGS. 7 and 8 showing insertion of the screw fastener 38. The intermediate shank portion 46 of the fastener includes an annular flange 78 having an outer diameter dimensioned for a sliding fit within the small diameter bore 72. The flange 78 is axially spaced between the head portion 44 and the threaded portion 40 of the fastener so as to axially define a shank region 80 of minimum diameter and structuraly weakest cross-section to which implant rupture is thereby limited. Further, the shank region 80 forms a seat for the washer 48 which is made of a deformable material such a silicone.

FIG. 7 shows the washer 48 in an undeformed condition during installation of the fastener 38 as the flange 78 becomes aligned with shoulder 74 between bores 56 and 72 in the post. Threaded insertion of the fastener is effected by torsion applied to the head portion 44 by means of a tool 82, for example, as shown in FIG. 7 resulting in an axial compressive force being exerted by the head portion on the washer 48 for axial displacement thereof with the head portion through bore 56. When the washer 48 engages the shoulder 74 as shown in FIG. 7, continued threaded insertion of the fastener causes the head portion to compress the washer, as shown in FIG. 8, as the flange 78 is axially displaced from the shoulder 74. In its fully compressed and deformed condition as shown in FIG. 8, the washer 48 will maintain the head portion axially spaced from shoulder 74 and establish fluid sealing contact with both the screw fastener made of metal and the ceramic post.

Such contact through the washer 48 is far superior from a fluid sealing standpoint than the imperfect sealing contact that would be otherwise established between the head portion 44 and the post at shoulder 74. Accordingly, effective fluid sealing of the interface region from the access bore 56 in the post is realized when the fastener 38 is fully inserted. The implant is finished by filling of the access bore 56 with resin 58 as hereinbefore described with respect to FIG. 1.

Figure 9:
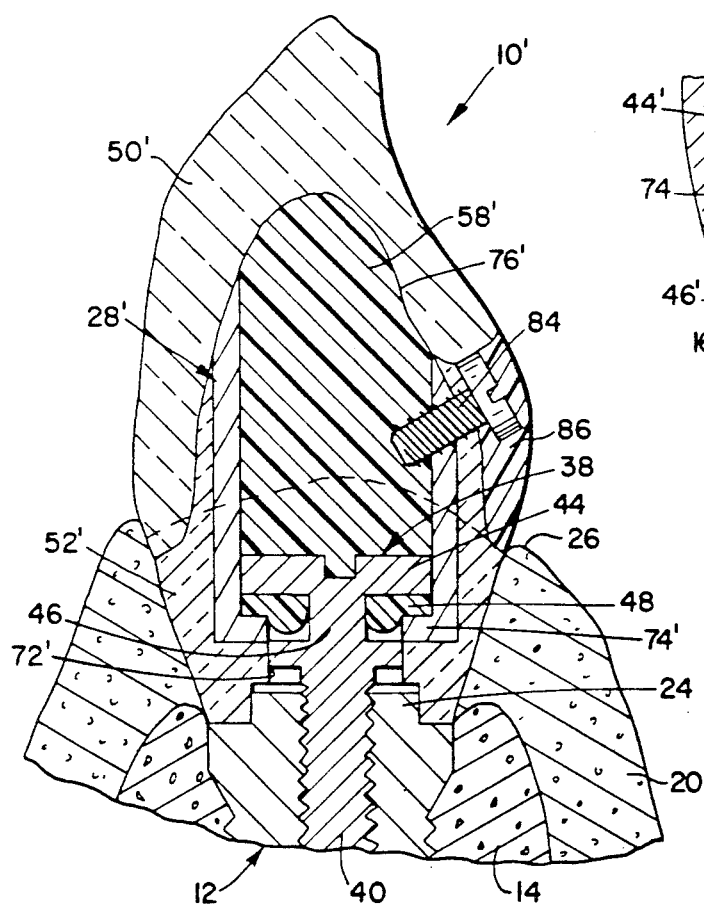
FIG. 9 is a section view of a dental implant installation in accordance with another embodiment of the invention.

FIG. 9 illustrates another installational embodiment of the present invention which is similar to that illustrated in FIG. 1 in so far as the assembly 10' of FIG. 9 is associated with a titanium implant fixture 12 threadedly embedded in the endentulous bone 14 so that its receiving end portion 24 is exposed to the interface region within the gum tissue 20. The same type of screw fastener 38 may also be threadedly inserted into the implant fixture 12 with a sealing washer 48 carried on the intermediate shank portion 46 of the screw fastener. However, an aluminum oxide support post 28' that is of a tubular cylindrical shape throughout is utilized. The trans-tissue end of post 28' has an annular shoulder flange 74' thereon axially spaced from the head 44 of the screw fastener by the deformed washer 48 to seal the interface region otherwise in communication with the small diameter bore 72' within an anatomically contoured or sculptured porcelain coping 52' surface bonded to the trans-tissue section of the ceramic post 28'.

With continued reference to FIG. 9, it will be observed that the end of the supragingival core section of the post 28' is cut to a contoured open end shape 76' through which the fastener 38 is inserted before a supragingival structure, including a restorative tooth 50', is fitted thereon. An additional screw fastener 84 may be utilized to secure such supragingival structure to the core portion of the post 28' at an angle to its longitudinal axis as shown. Also, resin filler 58' may be utilized to cover screw head 44 and fill the space within the bore of post 28' before the restorative tooth 50' is applied and attached, after which the assembly 10' is finished by filling the opening in the supragingival structure, exposing screw 84, with a resin filler 86.

Figure 10:
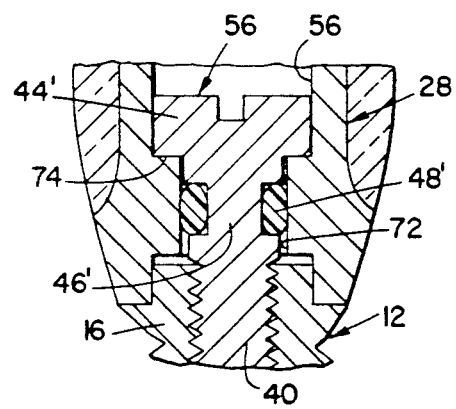
FIG. 10 is a partial section view similiar to that of FIG. 8, illustrating yet another embodiment of the invention.

According to the embodiment illustrated in FIG. 10, the screw fastener and washer described with respect to FIGS. 1-9 has been modified somewhat. A washer 48' as shown in FIG. 10 is retained on a minimum diameter portion 46' of the screw fastener 38' axially spaced from both the head portion 44' and the threaded portion 40' of the fastener. The head portion 44' accordingly abuts the shoulder 74 between the large and smaller diameter bores 56 and 72 of the abutment post 28 when the fastener 38' is fully inserted as shown in FIG. 10. The washer 48' will then be disposed in a compressed condition on the narrow diameter portion 46' of the fastener within bore 72 of the post 38' to effectively seal the gum tissue region within which the post is interfaced with the implant fixture 12.

Further, it will be appreciated by persons skilled in the art that various deviations from the described embodiments of the invention are possible and that many modifications and improvements may be made within the scope and spirit of the invention. Thus, it will be understood that the invention is not limited by the specific embodiments described, but only by the scope and spirit of the appended claims.

We claim:

1. In a dental implant including a metallic bone-embedded fixture having a receiving end portion, a support post, trans-tissue means on the post for abutment with the receiving end portion of the fixture said post having a supragingival core section extending from the trans-tissue means, a prosthesis, and a coping portion made of porcelain material through which the prosthesis is attached to the support post; the improvement residing in said support post being made entirely of a ceramic material, the coping portion covering the post and being surface bonded directly thereto by interaction between the ceramic and porcelain materials.

2. The dental implant as defined in claim 1 further including removable fastener means for securing the support post to the metallic fixture, said support post having an access bore from which the fastener means extends into the fixture through the receiving end portion thereof, and washer means deformed in response to threaded insertion of the fastener means into the fixture for sealing said access bore.

3. The dental implant as defined in claim 2 wherein said ceramic material of the support post is aluminum oxide.

4. The dental implant as defined in claim 3 wherein said coping portion is a separate piece completely covering the core section of the post.

5. The dental implant as defined in claim 1 wherein said trans-tissue means on the support post is an anatomically contoured formation on the coping portion.

6. In a dental implant including a metallic bone-embedded fixture having a receiving end portion, a support post, trans-tissue means on the post for abutment with the receiving end portion of the fixture within an interface region, said post having a supragingival core section extending from the trans-tissue means, a prosthesis, and a coping portion to which the prosthesis is attached received on the support post; the improvement residing in said support post being made of aluminum oxide, the coping portion covering the post and being surface bonded directly thereto, fastener means for securing the support post to the metallic fixture, said support post having an access bore from which the fastener means extends into the fixture through the receiving end portion thereof, and washer means deformed within the access bore in response to threaded insertion of the fastener means into the fixture for sealing said interface region, said coping portion being a separate piece made of porcelain material completely covering the core section of the post, said trans-tissue means comprising a conical formation intergral with the post while the supragingival core section includes a cylindrical portion and a curved transition surface portion interconnecting the cylindrical portion with the conical formation on the support post.

7. The dental implant as defined in claim 6 wherein the fastener means includes a head portion engaging the washer means in spaced relation to the receiving end portion of the fixture, a screw portion threadedly inserted into the fixture and an intermediate shank portion interconnecting the head and screw portions on which the washer means is retained, said intermediate shank portion having means for limiting dental implant rupture thereto.

8. In a dental implant including a metallic bone-embedded fixture having a receiving end portion, a support post trans-tissue means on the post for abutment with the receiving end portion of the fixture within an interface region, said post having a supragingival core section extending from the trans-tissue means, a prosthesis, and a coping portion to which the prosthesis is attached received on the support post; the improvement residing in said support post being made of a ceramic material, the coping portion covering the post and being surface bonded directly thereto, said trans-tissue means being a conical formation on the post while the supragingival core section includes a cylindrical portion and a curved transition portion interconnecting the cylindrical portion with the conical formation.

9. In a dental implant including a metallic bone-embedded fixture having a receiving end portion, a support post, trans-tissue means on the post for abutment with the receiving end portion of the fixture within an interface region, said post having a supragingival core section extending from the trans-tissue means, a prosthesis, and a coping portion to which the prosthesis is attached received on the support post; the improvement residing in said support post being made of a ceramic material the coping portion covering the post and being surface bonded directly thereto, fastener means for securing the support post to the metallic fixture, said support post having an access bore from which the fastener means extends into the fixture through the receiving end portion thereof, and washer means deformed within the access bore in response to threaded insertion of the fastener means into the fixture for sealing said interface region, the fastener means including a head portion in spaced relation to receiving end portion of the fixture, a screw portion threadedly inserted into the fixture and an intermediate shank portion interconnecting the head and screw portions on which the washer means is retained, said intermediate shank portion having means for limiting dental implant rupture thereto.

10. In a dental implant including a bone-embedded fixture including a receiving end portion exposed within an interfacing region between edentulous bone and gingival edge, a support post abutting the receiving end portion of the fixture within said interfacing region, said post having an access bore with an internal shoulder formed therein, and a prosthesis received on the support post, the improvement residing in: removable fastener means extending from the access bore into the fixture for securing the support post thereto in response to threaded insertion through said receiving end portion and washer means seated on the internal shoulder within the access bore for sealing the interface region in response to deformation by the fastener means during said threaded insertion of the fastener means.

11. The combination as defined in claim 10 including a coping portion embedded in the prosthesis and surface bonded directly to the support post and a filler occupying the access bore in covering relation to the fastener means.

12. In a dental implant including a bone-embedded fixture having a receiving end portion exposed within an interfacing region between edentulous bone and gingival edge, a support post, abutting means on the post for engagement with the receiving end portion of the fixture within said interfacing region, said post having an access bore formed therein, a prosthesis received on the support post, removable fastener means extending from the access bore into the fixture for securing the support post thereto in response to threaded insertion through said receiving end portion and washer means deformed within the access bore in response to said threaded insertion of the fastener means for sealing the interfacing region, the fastener means including a head portion engaging the washer means in spaced relation to the receiving end portion of the fixture, a screw portion threadedly inserted into the fixture and an intermediate shank portion interconnecting the head and screw portions on which the washer means is retained, said intermediate shank portion having means for limiting dental implant rupture thereto.

13. A method for making a custom fitted dental appliance to be secured by a screw fastener to a metallic fixture having a receiving end portion exposed within an interface region between edentulous bone in which the fixture is embedded and a gingival edge, including the steps of: fitting an axially elongated abutment post made of ceramic material into said interface region; forming a superstructure shaped for external contact with the abutment post; cutting the abutment post to fit within the formed superstructure; surface bonding the formed superstructure to the cut abutment post; fastening the abutment post through an access bore therein to the embedded metallic fixture; sealing the interface region from the access bore; and plugging the access bore with a filler.

14. The method of claim 13 wherein said step of surface bonding includes firing the superstructure assembled on the cut abutment post to form a unitary body therewith.

15. The method of claim 14 wherein said ceramic material of the abutment post is aluminum oxide.

16. The method of claim 15 wherein said superstructure includes a separate coping portion surface bonded to the cut abutment post by said step of firing.

17. The method of claim 16 wherein said steps of fastening and sealing includes threadedly inserting into the fixture said screw fastener to deform a washer retained within the access bore.

18. The method of claim 13 wherein said ceramic material of the abutment post is aluminum oxide.

19. In a method of making a custom fitted dental appliance to be secured to an implant fixture having a receiving end portion exposed to an interface region formed in edentulous bone within which the fixture is embedded, the steps of: fitting a prosthesis support post into said region, said support post having an access bore therein; threadedly inserting a screw fastener into the implant fixture through the access bore to fasten the post to the fixture; said screw fastener having a head portion retained in the access bore; positioning a washer on the screw fastener within the access bore; and deforming the washer against the head portion in response to said threaded insertion of the screw fastener into the implant fixture.

20. In a dental implant for a restoration tooth, a bone-embedded fixture, a prefabricated support in abutment with the fixture and to which the restoration tooth is bonded and means for securing the support to the fixture, said prefabricated support being made entirely of ceramic material covered by the restoration tooth, said means for securing including a fastener and an access bore in the support from which the fastener extends into the fixture and means for locationally limiting dental implant rupture to the fastener within the access bore of the support.

21. In a dental implant for a restoration tooth, a bone-embedded metallic fixture, a prefabricated support in abutment with the fixture and to which the restoration tooth is bonded and fastener means extending from the support for securing thereof to the fixture, said prefabricated support being made entirely of ceramic material covered by the restoration tooth.

22. In a dental implant assembly including an implant fixture to be disposed in a jaw-bone with a threaded hole formed therein; an abutment screw screwed into the threaded hole and rigidly supported therein; and a coping section attached to the abutment screw, an apparatus for supporting the coping section and sealing the abutment screw on the implant fixture, comprising a cylindrical post surrounding the abutment screw, and annular means surrounding the abutment screw between said cylindrical post and the implant fixture for sealing the cylindrical post against the implant fixture.

23. The apparatus as defined in claim 22 wherein said cylindrical post includes an interfacing portion and is made entirely of ceramic material.

24. The apparatus as defined in claim 23 wherein said annular means is a flexible washer.

25. The apparatus as defined in claim 22 wherein said annular means is a flexible washer.

26. In a dental implant assembly for supporting a dental prosthesis including an implant fixture to be disposed in a jaw-bone with a threaded hole formed therein, and an abutment screw screwed into the threaded hole and rigidly supported therein, an apparatus for resiliently supporting and sealing the abutment screw against the implant fixture, comprising a one-piece cylinder unit including a lower cylinder section surrounding the abutment screw and an upper cylinder section to be attached to the dental prosthesis, and annular flexible means surrounding the abutment screw for sealing said cylinder unit against the implant fixture.

27. Apparatus according to claim 26, wherein said lower cylinder section has an inside diameter larger than the outside diameter of the abutment screw, defining a space therebetween, and said annular flexible means being disposed in said space with a portion thereof between said lower cylinder section and the implant fixture.

* * * * *